(12) United States Patent
Perichaud et al.

(10) Patent No.: US 6,251,967 B1
(45) Date of Patent: Jun. 26, 2001

(54) ANTIMICROBIAL POLYMERS COMPRISING QUATERNARY AMMONIUM GROUPS, THEIR USE FOR MAKING A MATERIAL WITH ANTIMICROBIAL PROPERTIES AND METHODS FOR PREPARING THEM

(75) Inventors: Alain Perichaud; Florence Bataille; Christophe Baudrion, all of Marseilles; Lionel Panaiva, Aix en Provence, all of (FR)

(73) Assignee: Catalyse (Sarl) Limited Company, Marseilles (FR)

( * ) Notice: Subject to any disclaimer, the term of this patent is extended or adjusted under 35 U.S.C. 154(b) by 0 days.

(21) Appl. No.: 09/331,576
(22) PCT Filed: Dec. 30, 1997
(86) PCT No.: PCT/FR97/02459
§ 371 Date: Jun. 30, 1999
§ 102(e) Date: Jun. 30, 1999
(87) PCT Pub. No.: WO98/29463
PCT Pub. Date: Jul. 9, 1998

(30) Foreign Application Priority Data

Dec. 30, 1996 (FR) .................................................. 96 16362

(51) Int. Cl.⁷ .............................. C08K 6/00; C08K 20/10
(52) U.S. Cl. .................. 523/122; 525/329.4; 525/329.5; 525/329.7; 525/330.1; 525/330.5
(58) Field of Search ............................. 523/122; 524/460, 524/522, 555; 525/329.4, 329.7, 330.5, 330.1, 329.5; 528/486, 492

(56) References Cited

U.S. PATENT DOCUMENTS

| 3,872,128 | * | 3/1975 | Byck ................................. 260/286 R |
| 4,705,695 | * | 11/1987 | Lehmann et al. ......................... 427/3 |
| 5,057,579 | | 10/1991 | Fock et al. . |
| 5,133,970 | | 7/1992 | Petereit et al. . |
| 5,145,914 | * | 9/1992 | Esselborn et al. ................. 525/329.5 |
| 5,624,963 | * | 4/1997 | Mandeville, III et al. .......... 576/290 |
| 5,639,843 | * | 6/1997 | Babirad et al. ........................... 528/9 |

FOREIGN PATENT DOCUMENTS

| 4022651 | 1/1992 | (DE) . |
| 0187281 | 7/1986 | (EP) . |
| 03855627 | 9/1990 | (EP) . |
| 0525751 | 2/1993 | (EP) . |
| 0610955 | 8/1994 | (EP) . |
| 2010851 | 7/1979 | (GB) . |
| 2273934 | 6/1994 | (GB) . |
| 91/18027 | 11/1991 | (WO) . |
| 94/27620 | 12/1994 | (WO) . |

\* cited by examiner

*Primary Examiner*—Edward J. Cain
*Assistant Examiner*—Lee K Wyrozebski
(74) *Attorney, Agent, or Firm*—Dennison, Scheiner, Schultz & Wakeman

(57) ABSTRACT

The invention relates to antimicrobial non-cross-linked polymers which are constituted of an ester and/or amide resin to which quaternary ammonium salts are bound by a covalent bond which is potentially reactive with water, the quaternary ammonium content being at least 1 M/kg, a well as to the use thereof for the preparation of a material having antimicrobial properties and to their methods of preparation.

22 Claims, No Drawings

ANTIMICROBIAL POLYMERS COMPRISING QUATERNARY AMMONIUM GROUPS, THEIR USE FOR MAKING A MATERIAL WITH ANTIMICROBIAL PROPERTIES AND METHODS FOR PREPARING THEM

BACKGROUND OF THE INVENTION

The invention relates to antimicrobial non-cross-linked polymers which comprise quaternary ammonium groups bound via a bond which is potentially reactive with water, and which have an antimicrobial activity, especially an antibacterial activity.

The invention also relates to their methods of preparation as well as to their applications, especially in a non-limiting manner, for obtaining antibacterial materials having self-smoothening, self-sliding or anti-static properties or as binders for coatings or paints.

Obtaining polymers which comprise quaternary ammonium groups is described in a certain number of patents or patent applications.

WO 95/27473 describes a polymer having a carbon skeleton, which comprises quaternised nitrogen atoms, one of the substituents of which is hydrophobic and has at least eight carbon atoms, and having an antiperspirant activity.

DE 4 242 082 describes copolymers of acrylamide or methacrylamide which comprise quaternary ammonium groups the content of which must not exceed 20% of the mass of the final product.

EP 0 611 782 describes a homo- or copolymer which contains antimicrobial quaternary ammonium groups, but which comprise, between the polymer chain and the active group, one or more silicon-carbon or silicon-oxygen bonds which give the final product its particular properties.

WO 91/09915 describes an anti-fouling composition which is constituted of a hydrolysable binder, and which contains sulphonic acid groups and quaternary ammonium salts (the latter two being bound by an ionic and non-covalent bond).

EP 0 270 465 relates to quaternary ammoniums which are grafted onto a chlorinated vinylic resin by a non-hydrolysable or non-water sensitive bond.

EP 0 156 632 describes a copolymer which comprises acrylic or methacrylic esters which can optionally contain quaternary ammonium functions, and which contain organotin compounds which are introduced by copolymerisation, in a submarine anti-fouling paint application.

WO 84/02915 describes polymers comprising acrylic or methacrylic esters comprising units which are able to be hydrolysed and optionally able to contain quaternary ammonium functions, in a submarine anti-marking paint application.

Other publications, notably EP 0 494 554, EP 0 657 478, and EP 0 373 852, relate to quaternary ammoniums (mainly having a short chain of less than 4 carbons) bound to an acrylic skeleton. However, these documents describe products which are cross-linked and sometimes copolymerised with other vinylic monomers. In every case, the quaternary ammonium content is low.

SUMMARY OF THE INVENTION

It has now been found that polymers comprising quaternary ammoniums in a predominant amount possess an anti-microorganisms activity, in particular an antibacterial activity, which is optimal. Moreover, due to the potentially hydrolysable nature of the bond (of the amide or ester type) of the quaternary ammonium groups with the resin, they are susceptible of conferring a self-regenerating nature to the materials or coatings which contain them.

DETAILED DESCRIPTION OF THE INVENTION

According to a first aspect, therefore, the invention relates to non-cross-linked polymers, characterised in that they are constituted of an ester and/or amide resin to which quaternary ammonium salts are bound by a covalent bond which is potentially reactive with water, and in which the quaternary ammonium content is at least 1 mole/kg, preferably at least 2 moles/kg and in particular at least 3 moles/kg, for the use thereof as antimicrobial agents, notably as antibacterial agents.

In a preferred aspect, the weight percentage of quaternary ammonium salts is at least 80%, and advantageously up to 100% of the mass of the polymer.

In a particular aspect therefore, the invention relates to non-cross-linked polymers, characterised in that they are constituted of an ester and/or amide resin, to which quaternary ammonium salts are bound by a covalent bond which is potentially reactive with water, of general formula (I):

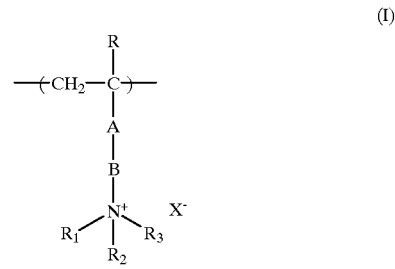

in which:

A represents a

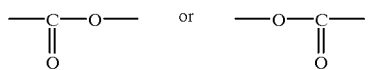

function,
and/or an amide function:

R represents H or $CH_3$;

B represents a $C_0$–$C_5$ alkylene chain, which is linear or branched, or an arylene or arylalkylene group;

$R_1$ and $R_2$, which are identical or different, each represent a $C_1$–$C_5$ alkyl chain $R_3$ represents a $C_8$–$C_{20}$ alkyl chain or an aryl or arylalkyl group $X^-$ represents an anion in which polymers the quaternary ammonium content is at least 1 mole/kg.

According to another aspect, the invention relates to non-cross-linked polymers, characterised in that they are constituted of an ester and/or amide resin to which quaternary ammonium salts are bound by a covalent bond which is potentially reactive with water, of general formula (II):

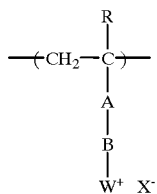

in which
A represents a

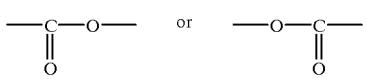

function, and/or an amide function:

R represents H or $CH_3$;
B represents a $C_0$–$C_5$ alkylene chain, which is linear or branched or an arylene or arylalkylene group;
$W^+$ is a saturated or unsaturated heterocycle comprising a nitrogen atom substituted with $R_4$, or directly bound to A or to B, and also able to contain, in addition to the quarternised nitrogen, one or more heteroatoms, which are identical or different,
$R_4$ represents a $C_1$–$C_{20}$ alkyl chain or an aryl or aralkyl group;
$X^-$ represents an anion;
in which polymers the quaternary ammonium content is more than 1 mole/kg Preferably, the total number of atoms of the heterocycle constituting $W^+$ is 3 to 15.

Advantageously, $W^+$ comprises a heterocycle selected from piperidine, piperazine, morpholine, thiomorpholine or thiazole, isothiazole, pyrazole, indole, indazole, imidazole, benzimidazole, quinoline, isoquinoline, benzotriazole, benzothiazole, benzoisothiazole, benzoxazole, benzoxazine, isoxazole, pyrrole, pyrazine, pyrimidine, pyridazine, quinazoline, acridine, one or more double bonds of which can be hydrogenated, it being possible for said groups to be non-substituted or substituted once or more, for example, in a non-limiting manner, with a substituent selected from the following groups: alkyl, halogen, cyano, nitro, hydroxy, sulphone, trifluoromethyl.

When B represents an arylene or arylalkylene group and/or $R_3$ is an aryl or arylalkyl group, the aromatic ring can for example be a phenyl group and the alkyl chain can be a $C_1$–$C_5$ alkyl chain.

According to an advantageous aspect, the invention relates to non-cross-linked polymers, characterised in that they are constituted of an ester and/or amide resin to which quaternary ammonium salts are bound by a covalent bond which is potentially reactive with water, comprising both units of formula (I) and (II) as defined above.

Advantageously, the polymers of formulae (I) and/or (II) above comprise a weight percent of quaternary ammonium salts of at least 80%, advantageously up to 100 % of the mass of the polymer.

This total weight percentage comprises the ester or amide functions as well as the mixture of the two types of functions.

In a preferred aspect, the quaternary ammonium content is greater than or equal to 2 moles/kg and notably greater than or equal to 3 moles/kg.

The anion $X^{-1}$ is selected from the anions which are usually used in the field and which are well-known to the person skilled in the art, such as, for example, in a non-limiting way, halogen, sulphate, phosphate, nitrate, cyano, tosylate or metal anions or organic anions, such as, for example, salicylate, benzoate, alkoxide, acetate, or undecylenate.

The invention also relates to the polymers of formulae (I) and/or (II) as defined above, for the use thereof as antimicrobial agents, notably as antibacterial agents.

According to a further aspect, the invention also relates to the use of the polymers described above, in particular of the polymers of formulae (I) and/or (II) for preparing proper objects with said polymers, in particular in the medical field for the preparation of medical materials such as, for example, catheters, gastric probes, blood collection pouches or even slabs for the ground, soles, tiling joints, or any object or material of which it is desirable to possess antimicrobial properties, notably antibacterial properties.

The invention also relates to the use of the polymers described above, in particular of the polymers of formulae (I) andlor (II) for the preparation of paints, not only marine paints, but also for white rooms for example, or even facade coatings, i.e. anywhere in fact where there are risks of development of microorganisms, and in particular bacteria, against which it is desired to protect oneself.

More particularly, the invention relates to paints or coatings which comprise, as a binder, at least one polymer described above, in particular at least one polymer of formulae (I) and/or (II), in combination with a volatile support. For this application, the polymers according to the invention are used in combination with the usual components of paints such as solvents in particular, for example an alcohol ether, xylene or cyclohexane, and pigments such as, for example, barium sulphate, titanium oxide or iron oxide.

The bond which is potentially reactive with water, i.e. hydrolysable, between the quaternary ammonium groups and the resin of the polymers according to the invention, presents an additional interest insofar as it enables the regeneration, layer by layer, of any material based on the polymer of formulae (I) and/or (II), whether it is presented in the form of a coating or as a constituting element of said material.

The invention also relates therefore to the use of the polymers of formulae (I) and/or (II) for the preparation of self-regenerating materials.

The invention also relates to the methods of preparation of the polymers described above.

2 main methods of preparation are characterised:
route 1) the modification of a polymer or of a copolymer by reaction with an alkyl halide;
route 2) the polymerisation or the copolymerisation of a monomer comprising a quaternary ammonium group.

The monomers which can be used to obtain the polymers of formula (I) in one or the other of the preparative routes, either with the view to their polymerisation or copolymerisation before quaternisation, or with the view to their prior quaternisation, are preferably selected from acrylates, methacrylates, ethylmehacrylate, ethyl methacrylates, butyl methacrylates, 2-ethylhexyl methacrylates, methoxyethyl methacrylates, acetates, acrylamides, methacrylamides, maleic anhydride and vinyl alcohol.

Monomers of the methacryloyl- or acryloylpyrazole type, which are known in the field, such as those described for example in Macromol. Chem., 186, 1985, 1605–161 1, will be used to obtain the polymers of formula (II).

According to a first variant of route 1 (route 1a), the chemical modification is carried out in one step on a polyacrylate-type polymer comprising a tertiary amine function such as, for example, 2-dimethylaminoethyl polymethacrylate or poly(3-dimethylarinopropyl methacrylamide). These precursors are obtained by methods of polymerisation which are known in the field. After dissolution of these polymers in polar-type solvents, such as, for example, methanol, propylene glycol monomethyl ether or a water/acetone mixture, the tertiary amine functions can be quaternised by an alkyl halide according to Scheme 1a below, in which A, B, $R_1$, $R_2$ and $R_3$ are as defined in formula (I) and X represents a halogen atom:

Scheme 1a

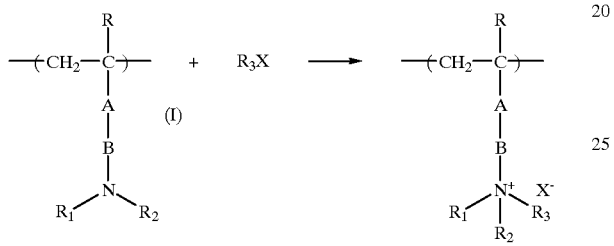

The alkyl halide represented by $R_3X$ comprises a long carbon chain which is linear or substituted with an aromatic ring, such as, for example, octyl, lauryl or benzyl bromide.

Route 1a can also be used for preparing the polymers of formula (II), by starting from a polyacrylate-type polymer comprising a tertiary amine function of formula:

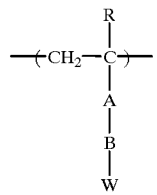

in which W represents a saturated or unsaturated heterocycle comprising a nitrogen atom, which may also contain, in addition to the nitrogen, one or more heteroatoms, which are identical or different.

In this case, the alkyl halide is represented by the formula $R_4X$, in which $R_4$ is as defined above for the formula (II).

The concentration of the initial polymer depends upon its weight molecular mass, which is between about 50,000 and about 100,000, and in general varies from 1 to 50% with respect to the whole of the solution, including the solvent. The concentration of alkyl halide is a function of the ammonium content desired and varies from 1 to 100% with respect to the number of moles of quaternisable tertiary amine. The reaction yields are of the order of 100% (calculated by coulometric determinations).

According to a 2nd variant of route 1 (route 1b), the chemical conversion can generally be carried out from poly(methyl methacrylate)-(PMMA)-type polymer by a transesterification with an alkanolamine which is quaternised beforehand. According to the reaction scheme 1b above in which B, R, $R_1$, $R_2$, $R_3$ and X are as defined in formula (I). The polymer is dissolved in a ketonic solvent such as, for example, methyl ethyl ketone, methyl isoamyl ketone or methyl isobutyl ketone at a concentration ranging from 1 to 50%. The quaternised ethanolamine is added in the cold with a catalyst such as, for example, dioctyl tin oxide.

Scheme 1b

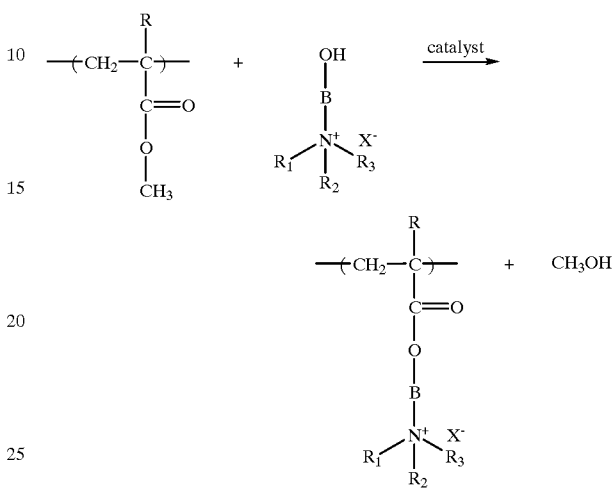

The solution is heated for 10 hours at 100° C. and the methanol formed is removed wit the aid of a Dean Stark-type apparatus. At the end of the experiment, a product is collected of which the ammonium content (per unit) is close to 100% according to the initial ratios.

According to a third variant of route 1 (route 1c), the chemical conversion can be carried out by esterification on poly(acrylic acid). This polymer is dissolved in the already-quaternised alkanolamine to which a reaction catalyst such as sulphuric acid for example, is added and a solvent such as toluene or cyclohexane which enables the water formed to be removed.

This variant is represented by the reaction scheme 1c below, in which B, $R_1$, $R_2$, $R_3$ and X are as defined in formula (I) and R=H.

Scheme 1c

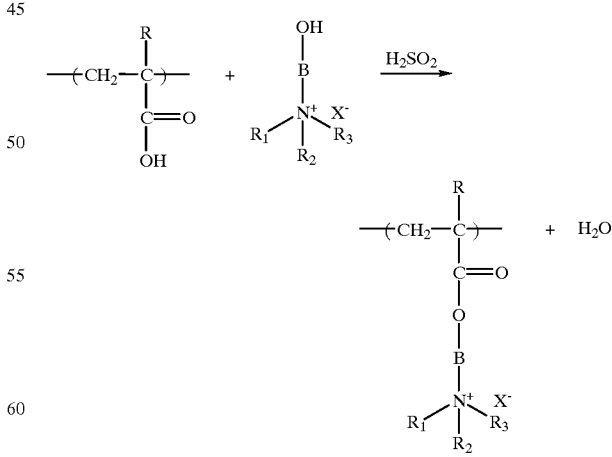

After 5 hours of azeotropic distillation at 130° C., a very viscous mixture is recovered (the weight molecular mass of which is greater than about 100,000) to which tetrahydrofuran is added. The fully quaternised polymer precipitates.

A fourth variant of route 1, which enables compounds of formula (I) to be obtained in which B, $R_1$, $R_2$ and $R_3$ are as defined above in formula (I) and R=H, consists in allowing a polyalcohol such as poly(vinyl alcohol) to react with a halogenated acid anhydride, notably a chlorinated acid anhydride, and then in allowing the ester function bearing the halogen atom to react with a tertiary amine to give the quaternary ammonium.

As indicated above, the second method of obtaining the polymers of formula (I) according to the invention comprising quaternary ammonium salts is the polymerisation of monomers comprising quaternary ammoniums, either in an organic solvent phase (route 2a), or in an aqueous phase (route 2b).

The monomers comprising quaternary ammoniums are firstly prepared by mixing, in an equimolecular amount, an amine of the methacrylic type or methacrylamide with an alkyl halide as defined above. The reaction temperature is maintained around 100° C. (the reaction is in homogeneous phase if an organic solvent is used, while initially it is heterogeneous if it is water). The pure product is recovered by evaporation of the solvent and recrystallised in the hot from tetrahydrofuran.

The polymerisation of the monomers comprising quaternary ammoniums can be carried out in an organic solvent phase by emulsion or solution (route 2a): in this case, azobisisobutyronitrile (AIBN) is added to the resulting product and heat is given at a temperature between about 20° C. and 200° C., preferably about 80° C. .

After 4 hours of reaction, the viscosity of the mixture very much increases and the solution is cooled to ambient temperature. The polymer can be used as such in a paint formulation.

When the polymerisation is carried out in an aqueous phase in solution or emulsion (route 2b), the monomers comprising quaternary ammoniums, which are soluble in water, are polymerised either by the addition of peroxide, such as, for example, AIBN or benzoyl peroxide, or with the aid of a redox-type initiator according to techniques which are known in the field, by heating at a temperature between about 20° C. and 120° C. Polymers having high weight molecular masses ($\geq 100,000$) can be obtained.

The resulting polymer precipitates and is then cooled and dried or, if it is desired to recover the polymer in an organic phase to use it directly in a paint formulation, the water can be removed by the addition of an azeotropic solvent such as an alcohol ether, e.g. monopropylene glycol monomethyl ether.

Reaction scheme 2 below, in which R, $R_1$, $R_2$, $R_3$, A, B and X are as defined above for formula (I), generally represents the 2n method of obtaining polymers of formula (I), namely quaternisation of the monomers and polymerisation.

Scheme 2

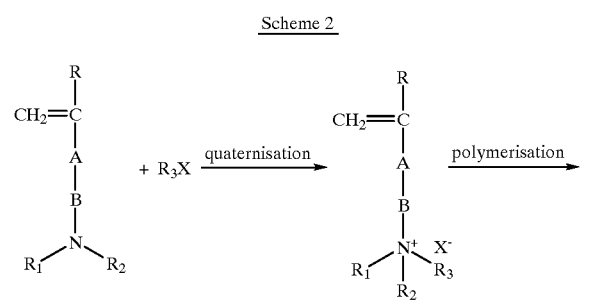

-continued

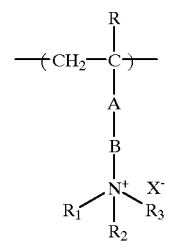

This reaction scheme can also be applied for the preparation of the polymers of formula (II), by starting with monomers of formula:

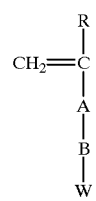

in which W is as defined above.

The invention is illustrated by the Examples below.

EXAMPLE 1

Chemical Modification of a Poly(2-dimethylaminoethyl Methacrylate) (Route 1a)

18.86 g (i.e. 0.132 mole) of poly(2-dimethylaminoethyl methacrylate) are introduced into a two-necked flask equipped with a condenser and a magnetic stirrer. 12.7 g (0.066 mole) of bromooctane and 36 g of acetone are then added. After 18 hours at 70° C., 30 g of propylene glycol monomethyl ether are then added and the acetone is distilled off. The final product is then produced with a dry extract of 51% which is ready to use in a marine paint formulation. A coulometric determination (as well as an analysis by infrared spectroscopy) indicates the presence of 2.03 moles of ammonium/kg of dry product.

EXAMPLE 2

Esterification of Poly(Acrylic Acid) (Route 1c)

20 g of ethanolamine (quatemised beforehand with bromooctane) are introduced in the cold with 5.1 g of poly(acrylic acid) (35% in water, the number molecular mass of which is 1,000 g/mole) into a 100 ml two-necked flask equipped with an azeotropic distillation apparatus (Dean Stark type) and a magnetic stirrer. 30 g of toluene and 1 ml of concentrated sulphuric acid are added to this mixture. The solution is then heated at 130° C. for 3 hours in which time 4 cm³ of water are collected.

After cooling, the polymer is recovered by precipitation in ether. The mass obtained (9 g) is analysed by infrared spectroscopy which indicates the presence of an ester carbonyl at 1730 cm$^{-1}$, i.e. 2.82 moles of ammonium/kg of dry product.

EXAMPLE 3

Modification of the Monomer and then Polymerisation in Organic Phase (Route 2a)

200 g of 2-dimethylaminoethyl methacrylate are added to 246 g of bromooctane in 450 g of propylene glycol monomethyl ether in a 3 liter reactor. After 3 hours of reaction at 80SC, a coulometric determination enables verifying a conversion rate of 100% into chloride ions. The quaternised monomer is then either purified by a precipitation in hexane, or used for a further step (polymerisation).

2 g of azobisisobutyronitrile are added to the solution resulting from the preceding step, and the temperature is allowed to rise progressively. After I hour 45 minutes (i.e. at a temperature of 76° C.), an increase in the viscosity is noted the reaction is then kept at this temperature for 3 hours. After cooling, a binder for paint is obtained the dry extract of which is 50%, i.e. 2.75 moles of ammoniumn/kg of dry product.

EXAMPLE 4
Modification of the Monomer and then Polymerisation in Aqueous Phase (Route 2b)

400 g of 2-dimethylaminoethyl methacrylate are added to 500 g of bromooctane and 200 g of water in a 3 liter reactor. At the start, the reaction medium which is heterogeneous is heated at 90° C. and the reaction is monitored by coulometric determination. After 4 hours of reaction, the conversion rate into chloride ions is 100% (the reaction phase is limpid and homogeneous). The product is cooled and can be used for the polymerisation.

400 g of a 1% aqueous solution of gum Arabic and 5 g of azobisisobutyronitrile are added to the aqueous solution of the preceding step. The mixture is brought to 80° C. After 1 hour of reaction, the viscosity of the mixture very much increases and a precipitate appears. After 2 hours at this temperature, the reactor is cooled to about 30° C. and the polymer which forms in the form of a whitish paste is dried under vacuum. After one week of drying, a white solid is obtained the analysis of which by infrared spectroscopy confirms the disappearance of the double bonds of the initial monomer and the presence of 2.75 moles of ammonium/kg of dry product. The product can then be dissolved in an organic solvent in order to obtain a binder for marine paint.

EXAMPLE 5
Preparation of a Polymer of Formula (II)
1) Preparation of the Monomer:

5 g of methacryloyl chloride (0.048 mole) are mixed with 100 ml of methyl ethyl ketone (MEK) in a 250 ml three necked flask equipped with stirring and a condenser. A solution of 4.8 g of 2-aminothiazole (0.048 mole) in 50 ml of MEK are added dropwise under mechanical stirring. At the end of the addition, the solution is heated at 60° C. for 4 hours. After cooling, 50 ml of basic water (sodium hydrogen carbonate) are added so as to neutralise the hydrochloric acid formed. 7.5 g of 2-thiazolylmethacrylamide are recovered after evaporation.
2) Modification of the Monomer and then Polymerisation (Route 2a)

5 g (0.030 mole) of 2-thiazolylmethacrylamide obtained in step 1) are added to 14 g of propylene glycol monomethyl ether and 4.26 g (0.030 mole) of iodomethane in a 100 ml two-necked flask equipped with a magnetic stirrer and a condenser. After 10 hours of reaction at 60° C., a coulometric determination indicates a conversion rate of 100% into iodide ions. The quaternised monomer is then either purified by precipitation in hexane, or used for the polymerisation step.

0.06 g of azobisisobutyronitrile are added to the solution obtained above under mechanical stirring, and the temperature is allowed to rise progressively to 85° C. After 4 hours at this temperature, an increase in the viscosity of the mixture is noted. After cooling the solution, a binder is obtained with a dry extract of 40% which is ready to use for a preparation of paint. The polymer can also be precipitated in pentane so as to obtain a polymer having an ammonium content of 3.22 moles/dry kg.

EXAMPLE 6
Study of the Antibacterial Properties of the Polymers According to the Invention The principle of determination is the placing of the resin which is a homopolymer having 100% quaternary ammoniums per constitutive unit (on a fixed surface) in contact with an known innoculum of a bacterial or fungal strain (Staphylococcus aurcus, Streptococcus faecalis, Escherichia coli, Pseudomonas aeruginosa or Candida albicans ) for a period of time of contact t (1 or 30 minutes).

The binder is poured into sterile wells and the solvent is then evaporated off under vacuum in the hot for one week. A known number of bacterial colonies is then placed in contact, and then a part is taken and placed in incubation for 48 hours. At this stage, the remaining colonies are then counted.

Polymer 1: N-octyl N,N-dimethylaminopropyl methacrylamide bromide

Polymer 2: N-dodecyl N,N-dimethylaminopropyl methacrylamide bromide

Polymer 3: N-hexadecyl N,N-dimethylaminopropylmethacrylamide bromide

Polymer 4: N-octyl N,N-dimethylaminopropylmethacrylamide chloride

Polymer 5: N-dodecyl N,N-dimethylamninopropylmethacrylamide chloride

Polymer 6: N-hexadecyl N,N-dimethylaminopropylmethacrylamide chloride

Polymer 7: N-octyl N-N-dimethyl aminoethylmethacrylate bromide (47%)–methacrylate (53%) copolymer Polymer 8: N-octyl N,N-dimethyl aminoethylmethacrylate bromide (65%)-methacrylate (45%) copolymer The results shown in Table 1 below are those of a determination carried out with an innoculum of Staphylococcus aureus, the initial number of colonies being $N_0 = 55.10^6$.

TABLE 1

| poly-mer n° | mass % of quaternary ammonium | quaternary ammonium content (mole/kg) | N = number of bacterial colonies remaining | | Log $(N_0/N_{30})$ |
|---|---|---|---|---|---|
| | | | t = 1 min | t = 30 min. $(N_{30})$ | |
| 1 | 100 | 2.75 | $0.75 \cdot 10^6$ | 100 | 5.7 |
| 2 | 100 | 2.39 | $48 \cdot 10^6$ | 0 | 7.7 |
| 3 | 100 | 2.11 | $3 \cdot 10^6$ | 75 | 5.9 |
| 4 | 100 | 3.14 | $0.02 \cdot 10^6$ | 30 | 6.3 |
| 5 | 100 | 2.67 | $2.1 \cdot 10^6$ | 23 | 6.4 |
| 6 | 100 | 2.32 | $1.1 \cdot 10^6$ | 0 | 7.7 |
| 7 | 47 | 1.33 | | $5 \cdot 10^6$ | 1.0 |
| 8 | 65 | 1.87 | | 120 | 6.5 |

The results show that the polymers in which the quaternary ammonium content is greater than 1 mole/kg possess a significant antibacterial activity.

What is claimed is:

1. An antimicrobial agent comprising a non-cross-linked polymer comprising a resin selected from the Group consisting of an ester resin, an amide resin, and an ester and amide resin, having a quaternary ammonium salt bonded thereto by a covalent bond which is potentially reactive with water, the quaternary ammonium salt being present in an amount of at least 1 mole/kg, and being at least one compound selected from the group consisting of:

a) a compound of the formula

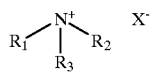

where $R^1$ is a $C_1$–$C_5$ alkyl chain, $R_2$ is a $C_1$–$C_5$ alkyl chain, $R_3$ is a $C_8$–$C_{20}$ alkyl chain or an aryl or arylalkyl group, and $X$ is an anion; and b) a compound of formula $W^+X^-$, where $W^+$ is a saturated or unsaturated heterocycle comprising a quaternized nitrogen atom substituted with a substituent $R_4$ or directly bonded to the polymer, where $R_4$ is a $C_1$–$C_{20}$ alkyl chain or an aryl or alkylaryl group, and $X^-$ is an anion.

2. Non-cross-linked polymer comprising a resin selected from the group consisting of an ester resin, an amide resin, and an ester and amide resin, having a quaternary ammonium salt bonded thereto by a covalent bond which is potentially reactive with water, the quaternary ammonium salt being present in an amount of at least 1 mole/kg, the polymer having a general formula (II):

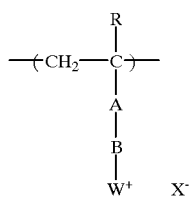

(II)

where $W^+$ is a saturated or unsaturated heterocycle comprising a quaternized nitrogen atom substituted with a substituent $R_4$, or directly bonded to the polymer, and where $R_4$ is a $C_1$–$C_{20}$ alkyl chain or an aryl or alkylaryl group, and $X^-$ is an anion.

3. Agent according to claim 1, wherein the quaternary ammonium content of the polymers is at least 2 moles/kg.

4. Agent according to claim 3, wherein when B represents an arylene or arylalkylene group and/or $R_3$ is an aryl or arylalkyl group, the aromatic ring is a phenyl group and the alkyl chain is a $C_1$–$C_5$ alkyl chain.

5. Agent according to claim 1, wherein characterised in that the weight percentage of quaternary ammonium salt is at least 80% of polymer weight.

6. Agent according to claim 5, wherein the weight percentage of quaternary ammonium salt is 100% of polymer weight.

7. Agent according to claim 1, wherein the polymer is selected from the group consisting of N-octyl N,N-dimethylaminopropylmethacrylamide bromide, N-dodecyl N,Ndimethylaminopropyl methacrylamide bromide, N-hexadecyl N,Ndimethylaminopropylmethacrylamide bromide, N-octyl N,N-dimethylaminopropylmethacrylamide chloride, N-dodecyl N,N dimethylaminopropylmethacrylamide chloride, N-hexadecyl N,Ndimethylaminopropylmethacrylamide chloride, N-octyl N-N-dimethyl aminoethylmethacrylate bromide (47%)-methacrylate (53%) copolymer, and N-octyl N,N-dimethyl aminoethylmethacrylate bromide (65%)-methacrylate (45%) copolymer.

8. Polymer according to claim 2, wherein that the weight percentage of quaternary ammonium salts is 80% of polymer weight.

9. Polymer according to claim 8, wherein that the weight percentage of quaternary ammonium salts is 100% of polymer weight polymer.

10. Paint comprising at least one polymer according to claim 2, as binder.

11. Facade coating comprising at least one polymer according to claim 2, as binder.

12. Object having antimicrobial properties comprising a polymer according to claim 2.

13. Object according to claim 12, which is a medical material.

14. A method for preparing a self-regenerating polymer comprising utilizing a polymer according to claim 2.

15. Agent according to claim 1, wherein said polymer is of general formula (I)

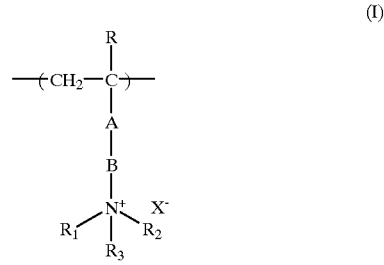

(I)

where A is function

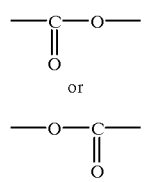

or

and/or an amide function of formula

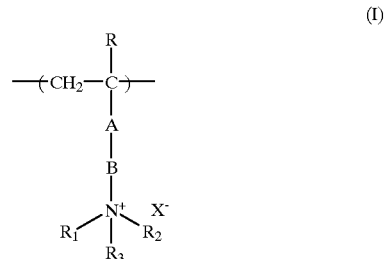

and R is H or $CH_3$, and B is a $C_0$–$C_5$ alkylene chain, which is linear or branched, or an arylene or arylalkylene group.

16. Polymer according to claim 2, additionally comprising units of formula (I):

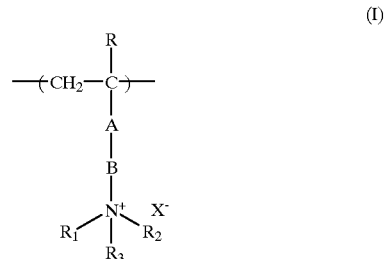

(I)

where A is function

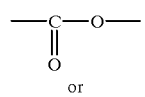

or

-continued

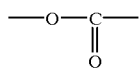

and/or an amide function of formula

and R is H or CH$_3$.

17. Polymer according to claim 2, wherein the quaternary ammonium salt is present in an amount of at least 2 moles/kg.

18. Polymer according to claim 16, wherein B is an arylene or arylalkylene group and/or R$_3$ is an aryl or arylalkyl group, and the group comprises an aromatic ring which is a phenyl group, and an alkyl chain which is a C$_1$–C$_5$ alkyl chain.

19. Polymer according to claim 2, wherein the heterocycle additionally comprises at least one further heteroatom.

20. Method for obtaining a polymer according to claim 2, comprising the step of reacting a monomer comprising a tertiary amine of formula:

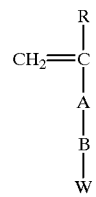

with an alkyl halide of formula R$_4$X, and polymerizing the reacted monomer.

21. Method according to claim 20, wherein the heterocycle additionally comprises at least one further heteroatom.

22. Agent according to claim 1, wherein the heterocycle additionally comprises at least one further heteroatom.

* * * * *